United States Patent
Forsberg et al.

(10) Patent No.: US 9,114,129 B2
(45) Date of Patent: *Aug. 25, 2015

(54) AUGMENTATION OF TITER FOR VACCINATION IN ANIMALS

(71) Applicant: OmniGen Research, L.L.C., Corvallis, OR (US)

(72) Inventors: Neil E. Forsberg, Corvallis, OR (US); Steven B. Puntenney, Ione, OR (US)

(73) Assignee: OmniGen Research, LLC, Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,327

(22) Filed: Jul. 30, 2014

(65) Prior Publication Data

US 2015/0024005 A1 Jan. 22, 2015

Related U.S. Application Data

(60) Continuation of application No. 14/155,730, filed on Jan. 15, 2014, now Pat. No. 8,828,402, which is a continuation of application No. 13/872,935, filed on Apr. 29, 2013, now Pat. No. 8,663,644, which is a continuation of application No. 13/400,520, filed on Feb. 20, 2012, now Pat. No. 8,431,133, which is a division of application No. 11/380,359, filed on Apr. 26, 2006, now Pat. No. 8,142,798.

(51) Int. Cl.

| | |
|---|---|
| *A61K 39/00* | (2006.01) |
| *A61K 39/02* | (2006.01) |
| *A61K 39/385* | (2006.01) |
| *A61K 39/39* | (2006.01) |
| *A61K 31/715* | (2006.01) |
| *A61K 31/716* | (2006.01) |
| *A61K 31/736* | (2006.01) |
| *A61K 35/02* | (2015.01) |
| *A61K 38/47* | (2006.01) |
| *A23K 1/16* | (2006.01) |
| *A23K 1/00* | (2006.01) |

(52) U.S. Cl.
CPC ............... *A61K 39/39* (2013.01); *A23K 1/008* (2013.01); *A23K 1/1631* (2013.01); *A61K 31/715* (2013.01); *A61K 31/716* (2013.01); *A61K 31/736* (2013.01); *A61K 35/02* (2013.01); *A61K 38/47* (2013.01); *A61K 39/02* (2013.01)

(58) Field of Classification Search
CPC .................................................. A61K 39/39
See application file for complete search history.

(56) References Cited

U.S. PATENT DOCUMENTS

| | | | |
|---|---|---|---|
| 3,943,250 A | 3/1976 | Richter et al. | |
| 3,961,080 A | 6/1976 | Sugimoto et al. | |
| 4,055,667 A | 10/1977 | Linton et al. | |
| 4,251,519 A | 2/1981 | Robbins et al. | |
| 4,287,179 A | 9/1981 | Amend | |
| 4,729,902 A | 3/1988 | Urman et al. | |
| 4,765,992 A | 8/1988 | Geneix et al. | |
| 5,149,549 A | 9/1992 | Beggs | |
| 5,165,946 A | 11/1992 | Taylor et al. | |
| 5,192,547 A | 3/1993 | Taylor | |
| 5,576,015 A | 11/1996 | Donzis | |
| 5,639,492 A | 6/1997 | Turk et al. | |
| 5,698,599 A | 12/1997 | Subbiah | |
| 5,814,346 A | 9/1998 | Gamberini | |
| 5,871,966 A | 2/1999 | Kofod et al. | |
| 5,922,373 A | 7/1999 | Johnston | |
| 5,935,623 A | 8/1999 | Alonso-Debolt | |
| 6,045,834 A | 4/2000 | Howes et al. | |
| 6,221,381 B1 | 4/2001 | Shelford et al. | |
| 6,344,221 B1 | 2/2002 | Evans | |
| 6,476,003 B1 | 11/2002 | Jordan et al. | |
| 8,142,798 B2 | 3/2012 | Forsberg et al. | |
| 8,431,133 B2 | 4/2013 | Forsberg et al. | |
| 8,568,715 B2 * | 10/2013 | Puntenney et al. | 424/94.61 |
| 8,663,644 B2 | 3/2014 | Forsberg et al. | |
| 8,828,402 B2 * | 9/2014 | Forsberg et al. | 424/184.1 |
| 8,834,868 B2 * | 9/2014 | Forsberg et al. | 424/94.61 |
| 2002/0048573 A1 | 4/2002 | Klock et al. | |
| 2005/0180964 A1 | 8/2005 | Puntenney et al. | |
| 2005/0220846 A1 | 10/2005 | Puntenney et al. | |
| 2006/0239992 A1 | 10/2006 | Puntenney et al. | |
| 2007/0202092 A1 | 8/2007 | Puntenney et al. | |

FOREIGN PATENT DOCUMENTS

| | | |
|---|---|---|
| DE | 4122906 | 2/1992 |
| EP | 0551331 | 11/1995 |
| EP | 0721741 | 7/1996 |
| JP | 07184595 A | 7/1995 |
| WO | WO 95/30022 | 11/1995 |
| WO | WO 97/02356 | 1/1997 |

OTHER PUBLICATIONS

Alexopoulos et al., Introductory Mycology, John Wiley & Sons, New York, Chapter 3, pp. 61-85, 1996.
AOAC Official Methods of Analysis of AOAC International, 16th Edition vol. 1, Chapter 4, p. 4 (4.1.10), AOAC Official Method 942.05 Ash of Animal Feed, 1997.

(Continued)

Primary Examiner — Albert Navarro
(74) Attorney, Agent, or Firm — Klarquist Sparkman, LLP

(57) ABSTRACT

The disclosure relates to a composition added to animal feed used in combination with a vaccine to enhance the effectiveness of the vaccine. Amongst other effects, the composition raises the titer of antibodies to the vaccine.

20 Claims, 9 Drawing Sheets

(56) References Cited

OTHER PUBLICATIONS

Burton, et al., "Gene expression signatures in neutrophils exposed to glucocorticods: A new paradigm to help explain "neutrophil dysfunction" in partureint dairy cows," *Vet Immunol Immunophathol.*, 2005, 15:105(3-4):197-219.
Catalano et al., "Small bowel infarction by *Aspergillus*." *Haematologica* vol. 82, pp. 182-183, 1997.
Chapman, *J. Animal Sci.* vol. 83, Suppl. 1, T177, 2005.
Charmley et al., "Mycotoxins: Their Origin, Impact and Importance . . . ," Proceedings of Alltech's Eleventh Annual Symposium, Edited by TP Lyon and KA Jacques, Nottingham University Press, pp. 41-63, 1995.
Civil Docket for Case {fourth root}: 3:06-cv-00153-JM-RBB, *Alltech, Inc. v. Cenzone Tech, Inc.*, U.S. District Court, Southern District of California (San Diego), Sep. 10, 2007.
Czop et al. "A beta-glucan inhibitable receptro on human monocytes, its identity with the phagocytic receptor for particulate activators of the alternative complement pathway," *J. Immunology*, vol. 134, pp. 2588-2593, 1985.
Deluyker et al., "Efficacy of an *Escherichia coli* J-5 mutant strain bacterin in the protection of calves from endotoxin disease caused by subcutaneous challenge with endotoxins from *Escherichia coli*," *Vaccine*, 23, pp. 709-717, 2004.
Derwent Publications Ltd, London, GB, XP002359382 & RU 2 115 421 C1 (Devichenskii V M) Jul. 20, 1998, abstract.
Derwent Publications Ltd, London, GB, XP002359383 & RU 2 093 162 C1 (as SIBE Biochem Int) Oct. 20, 1997, abstract.
Devegowda, Paper presented at African Lecture Tour "Mycotoxins in Feed," *Novel Biotechnological Solutions*, pp. 1-8, Mar. 10-15, 1997.
Dhabhar, "Enchancing versus Suppressive Effects of Stress on Immune Function: Implications for Immunoprotection and Immunopathology," *Neuroimmunomodulation*, 2009, 16:300-317.
First Office Action issued May 5, 2010, by the State Intellectual Property Office of the People's Republic of China for corresponding Chinese Patent Application No. 200780022219.X.
Fontaine, et al., "Molecular Organization of the Alkali-insoluble Fraction of *Apserigulls fumigatus* Cell Wall," *J Biol Chem*, vol. 275, pp. 27594-27607, 2000.
Fourth Office Action, dated Feb. 17, 2012, issued in corresponding China Patent Application No. 200780022219.X.
Frosco et al., Abstract F88, 89th meeting of the American Society for Microbiology, New Orleans, LA., May 14-18, 1989.
Galon, et al., "Gene profiling reveals unknown enhancing and suppressive actions of glucocorticoids on immune cells," *The FASEB Journal*, 2002, 16:61-71.
Hogan et al., "Efficacy of an *Escherichia coli* J5 Mastitis Vaccine in an Experimental Challeng Trial," *J of Dairy Science*, 75:415-422, 1992.
Information Disclosure Statement, Aug. 16, 2007, filed in reexamination of Patent No. 6,045,834 (Reexamination Control No. 90/008,406).
Information Disclosure Statement, Jun. 18, 2007, filed in reexamination of Patent No. 6,045,834 (Reexamination Control No. 90/008,406).
Information Disclosure Statement, Nov. 5, 2007, filed in reexamination of Patent No. 6,045,834 (Reexamination Control No. 90/008,406).
Information Disclosure Statement, Oct. 29, 2007, filed in reexamination of Patent No. 6,045,834 (Reexamination Control No. 90/008,406).
International Opinion PCT/US2005/028529, Jan. 16, 2006, pp. 1-5.
International Search Report PCT/US2005/028529, Jan. 16, 2006, pp. 1-4.
International Search Report and Opinion for PCT/US2007/066968 pp. 1-14. Oct. 8, 2007.
Jaeger et al., "Rapid Detection of *Candida, Aspergillus*, and *Fusarium* species in ocular samples using nested PCR," *J Clin Microbiol*, vol. 38(8), pp. 2902-2908, 2000.
Jensen et al., "Acute disseminated Aspergillosis in a cow with special references to penetration and spread," *J. Comp. Path.*, vol. 104, pp. 411-417, 1991.

Jensen et al., "The occurrence of fungi in bovine tissues in relation to portals of entry and environmental factors," *J Comp Path.*, vol. 107, pp. 127-140, 1992.
Keisler et al, Missouri Sheep Report, University of Missouri and Lincoln University, Nov. 1985.
Kessler, "Glucomannan-protein complexes from cell walls of yeasts," *Journal of Biological Chemistry*, 234(9); pp. 2281-2285, 1959.
King, et al., "A Targeted Glucocorticoid Receptor Antisense Transgene Increases Thymocyte Apoptosis and Alters Thymocyte Development," *Immunity*, 1995, 3:647-656.
Label, circa 2000, Cenzone Tech, Inc., Microbond.
Lyons, "Biotechnolgy in the Feed Industry," Proceedings of Alltech's Eleventh Annual Symposium, Edited by TP Lyons and KA Jacques, Nottingham University Press, pp. 129, 1995.
Magnoli et al., "The mycoflora and toxicity of feedstuffs from a production plant in Cordoba," *Mycotoxin Research* 18(1):7-22, Argetina, 2002
Mahesh et al., "Ability of Aflatoxin Binders to Bind Aflatoxin in Contaminated Poultry Feeds and Liquid Media in vitro," poster presented at Twelfth Symposium on Biotechnology in the Feed Industry, Apr. 1996.
Mayer, "Cytokines and Immunoregulation," *Immunoregulation and Cytokines*, Immunology-Chapter Thirteen, pp. 1-5, updated Jul. 2010, downloaded from http://pathmicro.med.sc.edu/bowers/immreg-ver2.htm on Nov. 13, 2012.
McCausland et al., "Mycotic abortion in cattle," *Australian Veterinary Journal*, vol. 64, No. 5, pp. 129-132, May 1987.
Ohsawa, "Clinical and patholigcial analysis of deep mycosis," Kansenshogaku Zasshi, vol. 65(2) pp. 200-208, Feb. 1991.
OminGen-AF product sheet, www.omingenresearch.com/feed.php/, Aug. 15, 2007.
OmniGen Research Update, vol. 3: Issue 5, 2005.
Patil et al, "Immune response of calves to bentonite and alum adjuvanted combined vaccine . . . ," *Indian Journal of Animal Sciences*, vol. 74, pp. 845-847, Aug. 2004.
Peppler, "Production of Yeasts and Yeasts Products," *Microbial Technology, Microbial Processes*, vol. 1, $2^{nd}$ Ed., pp. 157-185, 1979.
Prescott et al., "Fungal infections fo the small and large intestine," *J Clin Pathol.*, vol. 45(9) pp. 806-811, Sep. 1992.
Product Bulletin Cenzone Tech, Inc., Microbond, "The Proven Micotoxin Adsorbent that Aids in the Binding and Diminishing the Adverse Effects of Mycotoxins," pp. 8-14, Dec. 9, 2005.
Product Bulletin, Bill W. Perkins. Biotech Development Company, Inc., Dexter, Missouri, T-Bind pp. 1-18, 2000.
Product Bulletin, Ciendax S.A. Pronady 500, 100% yeast cell wall (*Saccharomyces cerevisiae*), pp. 1-4, circa 2000.
Proposed Pretrial Order, *Alltech, Inc. v. CenzoneTech, Inc.*, U. S. District Court for the Southern District of California, Civil Action No. 06-CV-01533 JM (RBBx), Jul. 31, 2007.
Puntenney et al, "Mycotic Infections in Livestock: Recent Insights and Studies on Etiology, Diagnosis and Prevention of Hemorrhagic Bowel Syndrome," Proceedings of the 18th Southwest Nutrition & Management Conference, Phoenix, Ariz., Feb. 20-21, 1989.
Ramirez-Montagut, et al., "Gluccorticoid-Induced TNF Receptor Family Related Gene Activation Overcomes Tolerance/Ignorance to Melanoma Differentiation Antigens and Enhances Antitumor Immunity," *The Journal of Immunolgy*, 2006, 176:6434-6442.
Rea, et al., "Glucocorticoids tranform CD40-triggering of dendritic cells into an alternative activation pathway resulting in antigen-presenting cells that secrete IL-10," *Immunobiology*, 2000, 95(10):3162-3167.
Rhodes et al., "*Aspergillus* and Aspergillosis," *Journal of Medical and Veterinary Mycology*, vol. 30, Supplement 1, 51-57, 1992.
Savage et al., "The Performance of Male Turkeys Fed A Starter Diet," Proceedings of Alltech's Twelfth Annual Symposium, Edited by TP Lyons and KA Jacques, Nottingham University Press, pp. 47-54, 1996.
Second Office Action issued Nov. 3, 2010, by the State Intellectual Property Office of the People's Republic of China for corresponding Chinese Patent Application No. 200780022219.X, 8 pp.
Specification Sheet, Cenzone Tech, Inc., A.I.P. Co., Ltd., Microbond, The proven microtoxin absorbent pp. 1-8, circa 2000.

(56) References Cited

OTHER PUBLICATIONS

Tangarone et al., "Purification and Characterization of an Endo-(1-3)-β-D-Glucanase from *Trichoderma longibrachiatum*," Applied and Environmental Microbiology. 55(1):177-184, 1989.

Tomee et al., "Putative virulence factors of *Aspergillus fumigatus*," *Clin Exp Allergy*, vol. 30(4) pp. 476-486, Apr. 2000.

Trenholm et al., "Mycotoxin Binding Agents: An Update on What We Know," Proceedings of Alltech's Twelfth Annual Symposium, Eds. TP Lvons and KA Jacques, Nottinqham, pp. 327-349, 1996.

Trenholm et al., "Mycotoxin Binding Agents: An Update on What We Know," *Zootecnica International*, pp. 40-42. Jan. 1997.

U.S. Department of Health and Human Services Food and Drug Administration Center for Veterinary Medicine, Guidance for Industry, Dioxin in Anti-Caking Agent Used in Animal Feed and Feed Ingredients, Oct. 1999.

Wang et al., *J. Anim. Sci.*, vol. 83, Suppl.1, Meeting Abstract 318, Jul. 2005.

Wang et al., Proceeding, Western Section American Society of Animal Science, vol. 55, pp. 349-352, 2004.

Wang, et al., "Ability of a commercial feed additive to modulate expression of innate immunity in sheep ummunosuppressed with dexamethasone," *Animal*, 2007, 1:945-951, doi:10.1017/S1751731107000365.

Xia et al., "The β-glucan-binding lectin site of mouse Cr3 (CD11b/CD18) and its function in generating a primed state of the recpetor that mediates cytotoxic activation in response to iC3b-opsonized target cells," *J. Immunol.* vol. 162, pp. 2281-2290, 1999.

\* cited by examiner

Control

Experimental

AUGMENTATION OF TITER FOR VACCINATION IN ANIMALS

CROSS REFERENCE TO RELATED APPLICATIONS

This is a continuation of U.S. application Ser. No. 14/155,730, filed Jan. 15, 2014, now U.S. Pat. No. 8,828,402, which is a continuation of U.S. application Ser. No. 13/872,935, filed Apr. 29, 2013, now U.S. Pat. No. 8,663,644, which is a continuation of application No. Ser. 13/400,520, filed Feb. 20, 2012, now U.S. Pat. No. 8,431,133, which is a divisional of U.S. patent application Ser. No. 11/380,359, filed Apr. 26, 2006, now U.S. Pat. No. 8,142,798, each of which is incorporated herein by reference in its entirety.

FIELD

The invention relates to combinations of a composition and a vaccine that augments titer of antibodies to the vaccine and methods for using the combination.

BACKGROUND

The immune response involves two distinct systems: the innate system and the acquired (antibody-mediated) system. The innate system is an evolutionarily ancient system that uses a variety of strategies to prevent infection. These include the epithelial cell barriers provided by skin, the gastrointestinal tract and the linings of the lung and mammary gland. In addition, the innate system includes the acidic barrier of the stomach (or abomasum in ruminant animals) and the digestive enzymes of the stomach, pancreas and small intestine. Finally, the innate system includes the white blood cells, macrophages and neutrophils. These cells first recognize pathogens via the presentation of unique markers on the surface of pathogens and then phagocytose and kill pathogens.

The innate system provides the initial immune response and provides the time required for the acquired antibody system to respond and to develop the antibodies needed to combat a specific pathogen. Usually one week to several weeks are required for a person or an animal to develop an antibody response. In this intervening time, an organism depends upon the innate system to hold off infection.

The acquired immune system may develop antibodies in response to a specific pathogen, toxin, chemical or any molecule that the organism recognizes as an antigen (i.e. the immune system recognizes the antigen as non-self). When pathogens infect a person or an animal, specific cellular markers associated with the pathogen are presented to antibody-producing cells. The acquired immune system then undergoes a process termed "clonal expansion". Specifically, this allows for the mass production of cells which produce antibodies which are directed toward a specific antigen associated with the pathogen.

Antibodies are synthesized by T-cells and B-cells. The T-cells mature in the thymus and present antibodies that are bound to their extracellular surfaces. The T-cells then circulate freely in blood and through lymphatic tissues. The binding of the T-cell to a pathogen via the bound antibody thereby results in the identification and subsequent destruction of the pathogen. In contrast, the antibodies produced by B-cells are secreted into the blood where they circulate freely. When B-cell-produced antibodies bind to a pathogen, they initiate a cascade of events which results in the identification and killing of the pathogen. Antibodies which are produced in response to immunization are classed into antibody isotypes.

The three most important antibody isotypes include IgM, IgG1 and IgG2. Other isotypes include, but are not limited to the IgA, IgD, IgG3, IgG4 and IgE isotypes and, within poultry, the IgY isotype.

The adaptive IgM response is the first antibody produced by T- and B-cells in response to an antigen; however, it is a relatively "weak" antibody with limited affinity for antigen and specificity. More "powerful" antibody responses are contained within the IgG1 and IgG2 isotypes; however, the development of the IgG1 and IgG2 isotypes requires longer periods of time. IgG isotype responses in pregnant individuals are particularly important as these are the antibody isotypes which are transferred from mother to offspring via colostrum at time of birth and which thereby transfer passive immunity to the newborn.

Vaccination (also called immunization) against disease is commonly practiced within the human medical and livestock industries. For example, to vaccinate against a pathogen, an animal is administered a vaccine in the form of non-infectious version of the pathogen or is administered only a portion of the pathogen. The acquired immune system responds by producing antibodies to the vaccine. If the animal is subsequently exposed to the live pathogen, the antibodies made in response to the vaccine are quickly mobilized and then recognize and target the pathogen for destruction.

The livestock industry relies upon immunization protocols against livestock-specific diseases to minimize morbidity and mortality arising from fungal, viral and bacterial infections. For example, in the dairy industry, it is common to vaccinate animals against *E. coli* as this is one of the most common forms of mammary gland infections (i.e. mastitis) and causes loss of production and, in severe cases, loss of the cow.

Several problems arise from current vaccination protocols. For example, the efficacy of vaccination protocols varies from individual to individual. Specifically, some individuals will develop a high titer (high serum concentration of antibodies) in response to a specific immunization protocol whereas others do not. As there is a direct correlation between the titer of an antibody and the immune system's response to an infection, some individuals remain susceptible to an infection by the pathogen even though they have been vaccinated. Consequently, there remains a need to improve the effectiveness of vaccines to reduce incidence of disease in animal populations.

SUMMARY

The disclosure relates to combinations for enhancing the effectiveness of vaccines and methods for using the combinations. The combinations of the disclosure use a composition that has the following constituents: $\beta$-1,3(4)-endoglucanohydrolase, $\beta$-1,3(4)glucan, silica, mineral clay and mannans. This composition is fed to animals that are about to undergo a vaccination protocol or are undergoing a vaccination protocol.

The combinations increase the effectiveness of the vaccine by increasing the serum concentration (titer) of antibodies to the vaccine. The increased serum concentration of antibodies remains even after the composition is withdrawn from the diet of the animals.

DETAILED DESCRIPTION

Figure 1:
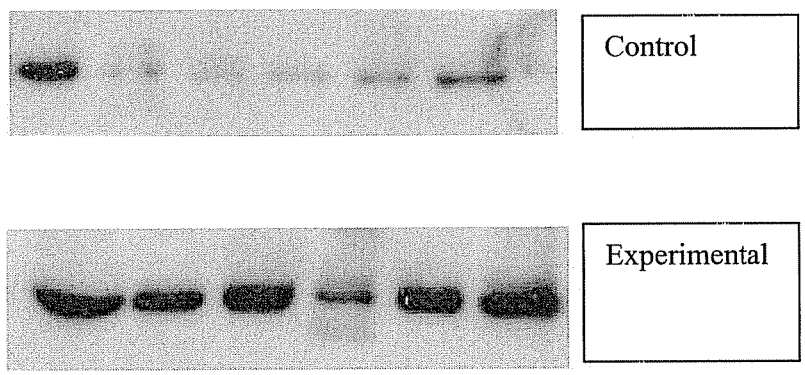
FIG. 1 shows results from Western blotting experiments that demonstrate the effect of the composition on the expression of neutrophil L-selectin as described in Example 1.

As required, detailed embodiments of the present composition are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present composition in virtually any appropriate manner.

The present disclosure is addressed to combinations that augment immune function in animals and methods for using the combinations. Generally, the combinations of the disclosure use a composition that has the following constituents: β-1,3(4)-endoglucanohydrolase, β-1,3(4)glucan, diatomaceous earth, mineral clay and glucomannan. The composition is used in combination with a vaccine such that the ingestion of the composition by the animal enhances the effectiveness of the vaccine. As defined here, a vaccine stimulates the immune system, including the production of antibodies when administered to an animal. One indication of an enhanced effectiveness of a vaccine is an increased titer of antibodies to the vaccine antigen in the serum of the animal.

The combination can be used effectively in feed for individuals or animals in many species such as mammals, including humans, and avians. In a preferred embodiment, the combinations are used in livestock mammals. The combinations can be used equally well with ruminants and non-ruminants. Examples of ruminants include but are not limited to cattle, sheep, goats, cows, deer, bison and buffalo. Non-ruminants include pigs, horses, sows and others. In a particularly preferred embodiment, the compositions of the composition are used for sheep and bovine livestock.

In one embodiment, the composition is fed to an animal during the period when the animal is undergoing a vaccination protocol. A typical vaccination protocol requires the administration of at least one and usually several doses of the vaccine over a defined period to maximize the stimulation of the immune system and the production of antibodies. In a preferred embodiment, the composition is fed daily to an animal starting before the initiation of the vaccination protocol and continuing after initiation of the vaccination protocol. In alternative embodiments, the composition may be fed to an animal starting after the initiation of the vaccination protocol or simultaneously with the initiation of the protocol.

The vaccine of the combination may elicit a response to a pathogen, a toxin, a drug or other molecules. The vaccine may be a DNA vaccine where a DNA molecule encoding an antigen is injected into an animal, resulting in synthesis of the antigen and subsequently an immune response to the antigen. In a preferred embodiment, the vaccine of the combination stimulates the production of antibodies to a disease causing pathogen. In a particularly preferred embodiment, the vaccine stimulates the production of antibodies against pathogens that cause mastitis. The J5 vaccine is one such commercially available mastitis vaccine (available from Pfizer).

Other examples of pathogens and diseases for which humans and animals are commonly vaccinated and which may benefit from a protocol which enhances efficacy include, but are not limited to, infectious bovine rhinotracheitis (IBR), parainfluenza type 3 (PI3), bovine virus diarrhea virus (BVDV), bovine respiratory syncytial virus (BRSV), rota virus, corona virus, *Campylobacter* spp., *Pasteurella* spp., pinkeye, *Salmonella* spp., *Clostridium* spp., *Leptospirosis*, Brucellosis, Newcastle disease, fowl pox, erysipelas, fowl cholera, Marek's Disease Virus (MDV), Infectious Bronchitis Virus (IBV), Avian encephalomyelitis, coccidiosis, rhinopneumonitis, equine influenza, *Streptococcus equi*, equine viral arteritis, equine monocytic ehrlichiosis, encephalomyelitis, West Nile encephalitis, rabies, parvovirus, adenovirus, Bordetella, Lyme disease, *Giardia*, pertussus, measles virus, hepatitis A and B, diphtheria, and poliomyelitis.

The constituents of the composition of the combination are prepared by methods commonly known in the art and can be obtained from commercial sources. The β-1,3(4)-endoglucanohydrolase is produced from submerged fermentation of a strain of *Trichoderma longibrachiatum*. The diatomaceous earth is available as a commercially-available acid-washed, product with 95% silica ($SiO_2$) and with its remaining components not assayed but consisting primarily of ash (minerals) as defined by the Association of Analytical Chemists (AOAC, 2002). β-1,3(4)glucan and glucomannan can be from commercial preparations of yeast cell wall extract derived from primary inactivated yeast (*Saccharomyces cerevisiae*) with the chemical composition shown in Table 1:

TABLE 1

| Moisture | 2-3% |
| --- | --- |
| Dry matter | 97-98% |
| Proteins | 14-17% |
| Fat | 20-22% |
| Phosphorus | 1-2% |
| Mannans | 22-24% |
| β-1, 3(4) glucans | 24-26% |
| Ash | 3-5% |

The mineral clays (aluminosilicates) used in this composition may be any of a variety of commercially-available clays including, but not limited to, montmorillonite clay, bentonite and zeolite.

In a preferred embodiment of the combination, β-1,3(4)-endoglucanohydrolase, diatomaceous earth, glucan and glucomannan, and mineral clay are combined weight to weight in the ranges from about 0.05-3%, 1-40%, 1-20% and 40-92%, respectively. In another preferred embodiment, β-1, 3(4)-endoglucanohydrolase, diatomaceous earth, glucan and glucomannan, and mineral clay are combined at 0.1-3%, 5-40%, 2-15% and 40-80%, respectively. In an especially preferred embodiment, β-1,3(4)-endoglucanohydrolase, diatomaceous earth, glucan and glucomannan, and mineral clay are combined at 0.2-3%, 20-40%, 4-10% and 50-70%, respectively.

In one embodiment, the composition is a dry, free-flowing powder which is suitable for direct inclusion into a commercially-available feed, food product or as a supplement to a total mixed ration or diet. The powder may be mixed with either solid or liquid feed or with water. In another embodiment, the composition is formed into pellets.

In one embodiment, when incorporated directly into feeds, the composition may be added in amounts ranging from about 0.1 to about 20 kg per ton (2000 pounds) of feed. In a preferred embodiment, the composition is added to animal feedstuffs or to food in amounts from about 0.5 kg to about 10 kg per ton of feed. In an especially preferred embodiment, the composition may be added to feeds in amounts ranging from about 1 to about 5 kg per ton of feed.

When expressed as a percentage of dry matter of feed, the present composition may be added to animal feedstuffs or to foods in amounts ranging from about 0.01 to about 2.5% by weight, preferably from about 0.0125% to about 2% by weight. In a preferred embodiment, the composition is added to animal feedstuffs or to food in amounts from about 0.05 to about 1.5% by weight, preferably from about 0.0625% to about 1% by weight. In an especially preferred embodiment, the present composition is added in amounts from about 0.1 to about 0.7% by weight, preferably from about 0.125% to about 0.5% by weight of feed.

Alternatively, the composition of the present combination may be fed directly to mammalian or *avian* animals as a supplement in amounts of from about 0.01 gram to about 1 gram per kilogram of live body weight, preferably from about 0.012 gram to about 0.5 gram per kilogram of live body weight, more preferably from about 0.016 gram to about 0.37 gram per kilogram of live body weight per day. In an especially preferred embodiment, the composition may be provided for use with many species in amounts of from about 0.05 grams to about 0.20 grams per kilogram of live body weight per day.

As examples, the composition may be provided to sheep in the range of from about 2 grams per head per day to about 8 grams per head per day. For bovine animals, the composition may be provided in the range of from about 10 grams per head per day to about 60 grams per head per day. One of skill and art can appreciate that the amount of the composition fed can vary depending upon the animal species, size of the animal and type of the feedstuff to which the composition is added.

Examples are now provided in order to illustrate the concepts of the composition with a certain degree of specificity.

EXAMPLE 1

An experiment was conducted with sheep with the goal of determining the ability of the composition to increase expression of neutrophil L-selectin, a marker of the innate immune system, in immunosuppressed animals. Animals (six per group) were divided into two groups: Control and Experimental. The Control group received a high energy ration consisting of chopped hay available *ad libitum,* 1 lb of ground corn per head per day and one lb of baked wheat mill run per head per day for a period of 28 days. During this time, they also received twice daily injections of dexamethasone, an immunosuppressive drug. The Experimental group received daily intake of the composition (5 grams per head per day) for 28 days and received the same diet and dexamethasone injection protocol as the Control. This composition of the Experimental group was 65.8 weight percent of mineral clay, 0.20 weight percent of endoglucanohydrolase, 9.0 weight percent of glucans and glucomannan, and 25 weight percent of calcined diatomaceous earth. At the end of the study, blood samples were recovered and neutrophils were purified using Percoll gradient centrifugation. The amounts of L-selectin expression in neutrophils were assessed using Western blotting techniques and antibodies specific for L-selectin.

As shown in FIG. 1, top panel, animals that did not receive the composition had low and variable expression of L-selectin. As shown in FIG. 1, lower panel, animals that received the composition demonstrated a consistent increase in L-selectin expression. The top panel represents six Control, immunosuppressed animals. The lower panel represents six Experimental immunosuppressed animals which received the composition in their diet.

EXAMPLE 2

In this study, the stimulation of the innate immune system in sheep was examined when the Experimental composition of Example 1 was provided in a pelleted diet. The basal diet consisted of 21.55% barley, 10.0% canola meal, 5% distillers grains, 40% ground corn, 1.50% limestone, 0.01% manganese sulfate, 0.01% microvitamin E, 4.0% molasses, 0.25% mono-cal, 0.25% potassium chloride, 0.60% sodium chloride, 0.03% sodium selenite, 15.79% wheat mill run, 0.01% zinc sulfate, 0.75% ammonium sulfate and 0.2 5% cobalt sulfate. When the Experimental composition was added to this diet, it was included at 0.6% replacing that portion of wheat mill run. Twenty-eight sheep were assigned to four treatments which consisted of a Control group, a group which received the Experimental composition in powdered form, a group which received the Experimental composition in pelleted form where pellets were formed at a temperature of 160° F., and a group which received the Experimental composition in pelleted form where pellets were formed at 180° F. All animals were immunosuppressed via daily injection of Dexamethasone.

Figure 2:
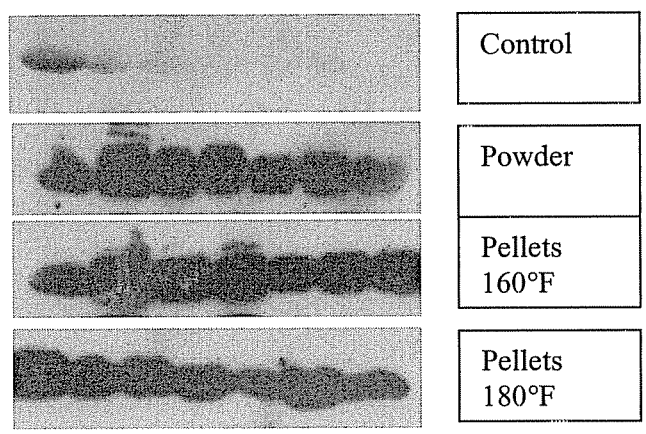
FIG. 2 shows results from Western blotting experiments that demonstrate the effects of the composition in unheated and heated (pelleted) forms on the expression of neutrophil L-selectin as described in Example 2.

The study was conducted using methods identical to Example 1 except the composition was administered in pellets that were manufactured by forming the pellets at high temperatures. The rationale for conducting this study was to determine whether heating of the composition (as is required in pellet formation) might inactivate the ability of the composition to augment innate immunity. As shown in FIG. 2, sheep (Control) which did not receive the composition expressed very low levels of L-selectin in neutrophils. The provision of the Experimental composition even in a pelleted (heated) form still increased expression of neutrophil L-selectin markedly.

In FIG. 2, the uppermost panel represents neutrophil L-selectin expression in immunosuppressed animals fed a control diet without the composition. The second panel (Powder) represents L-selectin expression in immunosuppressed animals which received the Experimental composition in unheated freely-mixed form as in Example 1 (Experimental group). Panels three and four represent neutrophil L-selectin expression in immunosuppressed animals which received the Experimental composition in pelleted forms. The pellets used in Panel 3 were formed by heating to 160° F. and Panel 4 pellets were heating to 180° F. during manufacture of the feeds.

EXAMPLE 3

An experiment was performed with rats to investigate whether the composition had ability to augment innate immunity in a non-ruminant model. In this study, rats were assigned to one of two treatments: a Control group (un-supplemented diet) and an Experimental group where the composition of Example 1 was added to the diet at 1% of dry weight of feed. In this experiment, rats were fed a commercial ground rat chow with or without the Experimental composition. Immunosuppression using dexamethasone injection protocols were not utilized in this study. Following 14 days, blood samples were taken from anesthetized rats via cardiac puncture. Neutrophils were isolated from blood samples using Percoll gradient centrifugation and total RNA was isolated using TriZol.

Figure 3:
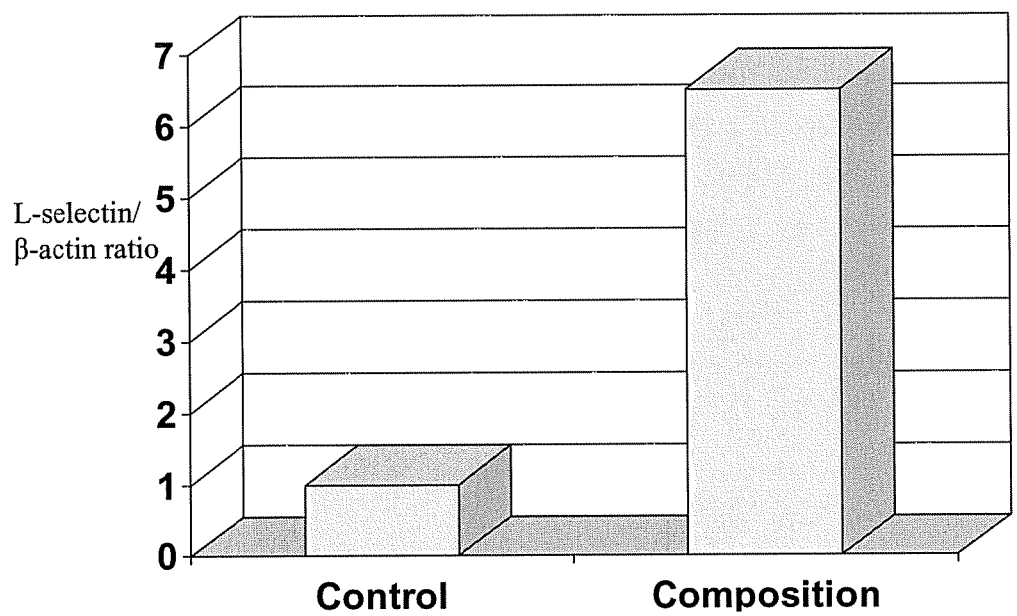
FIG. 3 is a graph summarizing the effects of the composition on the expression of the mRNA encoding L-selectin in rat neutrophils as described in Example 3.

The concentration of the messenger RNA (mRNA) encoding rat L-selectin in the neutrophil RNA samples was then determined by quantitative reverse transcriptase polymerase chain reaction (QRT-PCR) using primers which were specifically developed for assay of rat L-selectin. The amounts of L-selectin mRNA were standardized by showing them as a proportion of β-actin mRNA, which is expressed in all cells at a fairly constant level. As shown in FIG. 3, and in agreement with the results in Examples 1 and 2, the composition increased expression of L-selectin mRNA by greater than 6-fold ($P<0.05$).

This study demonstrated that the increased expression of L-selectin protein as shown in by Western blotting in Examples 1 and 2 may be caused by an increase in the mRNA encoding this protein. This implies that the composition alters the rate of transcription of the gene encoding L-selectin.

EXAMPLE 4

Neutrophils, cells of the innate immune system, are able to signal and thereby up-regulate the production of antibodies by the acquired immune system through the secretion of interleukin-1β (IL-1β). To investigate the ability of the composition to induce neutrophils to increase synthesis of IL-1β, the concentration was assessed of IL-1β in neutrophils taken from the same sheep as described in Example 1. To complete this study, Western blotting and antibodies specific for IL-1β were used.

Figure 4:
FIG. 4 shows results from Western blotting experiments that demonstrate the effects of the composition on the expression of neutrophil interleukin-1β (Il-1β) as described in Example 4.
Figure 4:

As shown in FIG. 4, animals which did not receive daily provision of the composition contained virtually undetectable levels of IL-1β; however, provision of the composition to animals caused a marked increase in the expression of IL-1β ($P<0.05$). In FIG. 4, the top panel represents six Control-fed immunosuppressed animals. The lower panel represents six Experimental composition-fed immunosuppressed animals which received the composition. Concentrations of IL-1β were determined using Western blot analysis and an antibody specific for IL-1β.

These data indicate that the composition possesses the ability to not only increase markers of innate immunity (e.g., L-selectin; Examples 1, 2 and 3) but to also increase expression of the key signaling molecule (i.e., IL-1β) that up-regulates the adaptive immune system.

EXAMPLE 5

The goal of this experiment was to determine which genes were differentially-expressed in neutrophils following the feeding of the composition to peri-parturient dairy cattle. In this study, the mechanism(s) by which the composition increased the expression of IL-1β in neutrophils was examined. Peri-parturient dairy cattle are a good model because the stress of pregnancy leads to immunosuppression, making the cows particularly susceptible to infection.

In this experiment eight peri-parturient dairy cattle were assigned to a Control diet that did not have the Experimental composition and eight cattle were assigned to an Experimental group that received the composition of Example 1 in their diet (56 grams per day per head). Animals were fed the diets for approximately 28 days until parturition. At 12-15 hours following parturition, 500 ml samples of blood were recovered via jugular puncture and neutrophils were prepared via large-scale Percoll gradient centrifugation.

RNA was isolated from neutrophils using the TriZol method and then reverse-transcribed into cDNA using reverse transcriptase. During reverse transcription, differently-colored nucleotide-based dyes (Cy3 and Cy5) were employed such that complementary DNAs (cDNAs) synthesized from the two different treatment (Control and Experimental) groups incorporated different colors. The cDNA samples from Experimental and Control groups were then applied to a BoTL-5 microarray slide. This microarray was prepared at the Center for Animal Functional Genomics at Michigan State University and contains 1500 genes (each arrayed in triplicate) upon a glass slide. The cDNAs generated from the Experimental and Control group samples were then allowed to compete for binding to the 1500 genes on the array and the relative expression of the genes was then assessed by comparing relative abundance of Cy3 and Cy5 signals on each spot on the array. Data were then statistically analyzed to identify those genes which were differentially-expressed (those genes where $P<0.05$).

The results showed that greater than 20 genes were differentially expressed ($P<0.05$) in bovine neutrophils taken from the Experimental group. Interleukin-converting enzyme (ICE) was one such up-regulated gene. This was confirmed using QRT-PCR and primers specific to the bovine ICE sequence. ICE is the rate-limiting enzyme in the conversion of inactive pro-IL-1β to the active, secreted IL-1β. Thus, the composition may up-regulate adaptive immunity (i.e., such as increasing antibody titer) through its ability to increase expression of neutrophil ICE activity and, consequently, secretion of IL-1β.

EXAMPLE 6

To test the hypothesis that the composition enhanced the effectiveness of a vaccine, the development of titer following a vaccination protocol was examined. Eighteen beef cattle (six cattle in each group) were assigned to one of three treatments: Control, Treatment 1, (15 grams of composition in the diet per head per day) and Treatment 2 (30 grams of composition per head per day). The diet of the animals consisted of a grass hay diet which was offered ad *libitum* with a daily supplement which provided 14% crude protein, 3% crude fat and 20% crude fiber (Table 2). Animals were provided with 12 pounds of this supplement per head per day throughout the trial. The Experimental composition of Example 1 was mixed directly into this supplement so that expected intakes of 15 grams per head per day and 30 grams per head per day were delivered to cattle in Treatment 1 and 2 respectively.

The animals were administered these diet treatments for 56 days after which the composition was withdrawn from the diet of Treatments 1 and 2. All animals were maintained on the same control diet without the composition until Day 84. On days 7, 21 and 35 of the experiment all animals were administered an *E. coli* J5 vaccine (Pfizer). This vaccination protocol (i.e., three injections, 14 days apart) followed manufacturer's recommendations. This vaccine is used commercially in the dairy industry as a means of reducing the likelihood of coliform mastitis. A limitation to this vaccine, and to most other vaccines, is the variable and limited response in titer.

Blood samples were taken using jugular puncture on Days 0, 14, 28, 42 and 56 on which day the composition was removed from the animals' diet. All animals remained on a common diet without the composition until day 84. Blood samples were also taken on Day 82 to determine whether any changes in titer induced by the composition were maintained following its withdrawal from the diet. Serum was prepared from all animals by centrifugation. Concentrations of antibodies specific for the E. coli J5 vaccination were assessed in three different immunoglobulin fractions (IgM, IgG1 and IgG2) using enzyme-linked immunosorbant assays (ELISAs). To assay E. coli J5 titers in the IgM, IgG1 and IgG2 immunoglobulin fractions, a culture of E. coli (obtained from Dr. Jeanne Burton, Center for Animal Functional Genomics, Department of Animal Sciences, Michigan State University) was grown, harvested and used to coat 96-well plates. Subsequently, serum samples (diluted 1:5000) from the animals were added to individual wells on the coated plates and allowed to incubate for one hour to allow the antibodies in the animal serum to bind to the E. coli J5 antigen. The ELISA plates were washed with phosphate-buffered saline (PBS) containing Tween-20.

Secondary antibodies (horseradish peroxidase (HRP)-conjugated ovine anti-bovine) that bound specifically either to bovine IgM, IgG1 or IgG2 (Beth Laboratories, Montgomery, Tex.) were added to the washed plates. The secondary antibodies were conjugated to horseradish peroxidase. Following incubation for an additional one hour with the secondary antibodies, the plates were washed again with PBS and Tween-20. The peroxidase substrate TMB (tetramethylbenzidine) was added to the plates and the resulting color reaction was quantitated by measuring the absorbance at 450 nm using an ELISA plate reader.

As shown in Table 3, the Experimental composition had no effect (at the threshold of $P>0.05$) on the development of E. coli J5 titer associated with the IgM antibody isotype. However, the composition stimulated and maintained J5 titer in IgG1 and IgG2 antibody isotypes as shown in FIGS. 5 and 6 and Tables 4 and 5.

Figure 5:
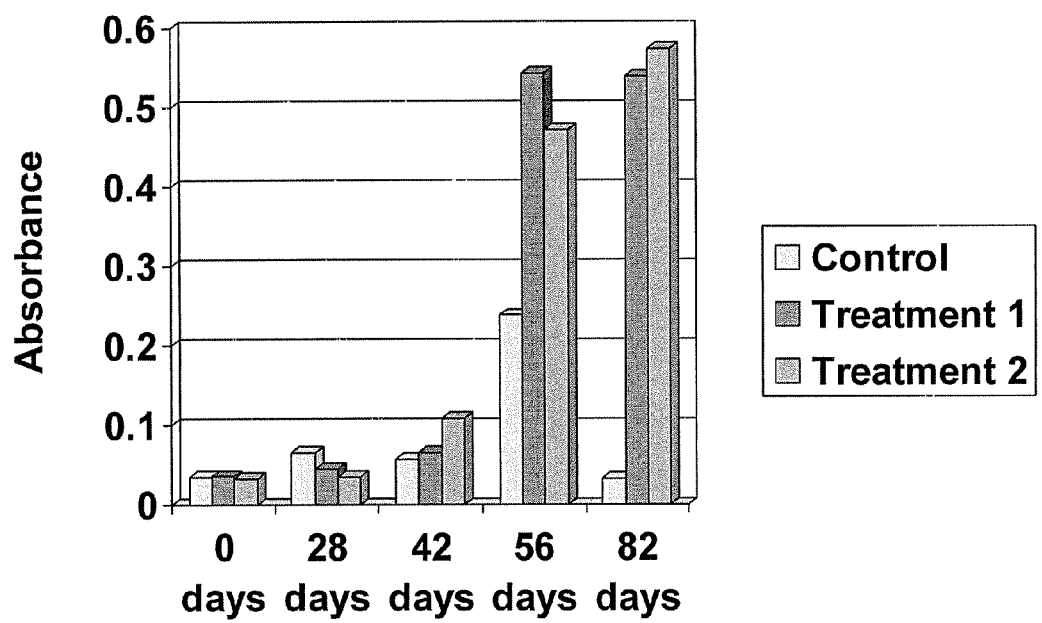
FIG. 5 is a bar graph that summarizes the results of ELISAs used to quantitate IgG1 titer against the J5 vaccine as described in Example 6.

The IgG1 titer increased on Day 56 ($P<0.05$) in animals which had received both Treatment 1 and Treatment 2 (Table 4 and FIG. 5). By Day 82, titer in Control animals had fallen back to pre-experiment (Day 0) levels. However, the animals which had been fed Treatment 1 or Treatment 2 had elevated J5 titer compared to the Control animals ($P<0.05$). In fact, animals which had received the Treatment 1 or 2 demonstrated no loss of IgG1 titer once the invention had been removed from the diet following 56 days (Table 4 and FIG. 5).

Figure 6:
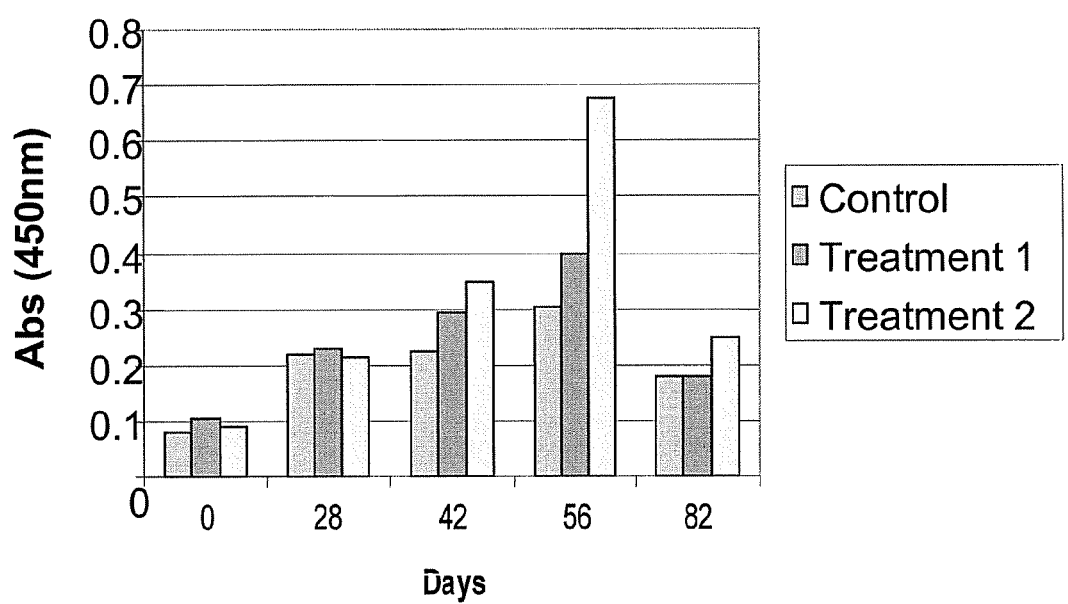
FIG. 6 is a bar graph that summarizes the results of ELISAs used to quantitate IgG2 titer against the J5 vaccine as described in Example 6.

As shown in Table 5 and FIG. 6, with respect to the IgG2 fraction, addition of 15 g per head per day (Treatment 1) or 30 g per head per day (Treatment 2) of the composition caused a step-wise increase in J5 IgG2 titer at 42 days (i.e. the higher dose increased titer by 57% and the low dose by 30% compared to the Control), although this effect was not statistically significant at $P<0.05$ (the P value was 0.16). Following 56 days, Treatment 2, (the higher dose of the Composition) caused a significant elevation in J5 titer ($P<0.05$). Treatment 1 (the low dose of the Composition) caused an elevation in J5 titer within the IgG2 fraction at this time point although this effect was not statistically significant at a threshold of $P<0.05$ (P value=0.12). On Day 82 of the study, after the Composition had been withdrawn from the diet, animals fed the higher dose of the Composition had an elevated titer within the IgG2 fraction (14% increase compared to the Control); however, this effect was not significant at the threshold of $P<0.05$ (P value is=0.09).

These data indicate that the Composition has the ability to increase titer of and, furthermore, to maintain titer in the IgG1 fraction following withdrawal of the composition from the diet ($P<0.05$). The Composition also has the ability to increase development of titer within the IgG2 fraction ($P<0.05$).

Figure 7:
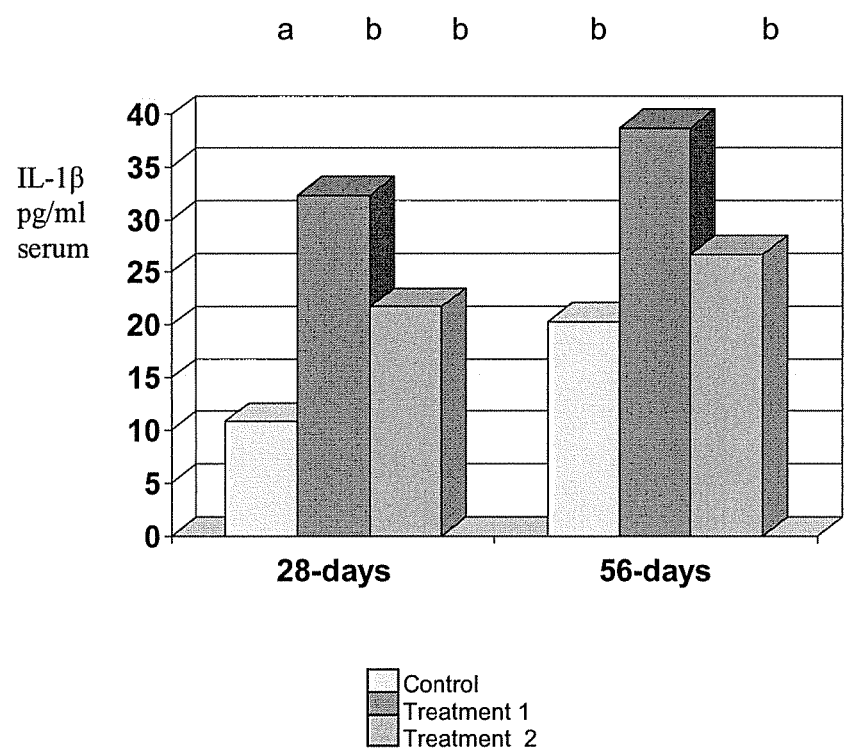
FIG. 7 is a bar graph that illustrates the effects of a low dose (15 grams/day) and high dose (30 grams/day) of the composition on the expression of interleukin-1β in beef cattle as described in Example 6.

IL-1β concentrations were also examined in the serum samples from the Control, Treatment 1 and Treatment 2 animals using an ELISA for IL-1β (R+D Systems Minneapolis, Minn.)). As shown in FIG. 7, results indicated that both Treatment 1 and Treatment 2 increased serum concentrations of IL-1β after 28 days. After 56 days, the low dose of the Composition also significantly elevated serum concentration of IL-1β ($P<0.05$). The high dose of the Composition caused a numerical elevation in serum IL-1β on Day 56 of the study; however, this effect was not significant at $P<0.05$ (P value=0.23). Although not wishing to be bound by theory, the composition may stimulate the innate immune system (e.g., via neutrophil activation) and neutrophils then stimulate the acquired immune system by secretion of IL-1β. IL-1β specifically increased ability of B-cells to increase the rate of development of IgG2 titer and maintains titer within the IgG1 fraction.

Figure 8:
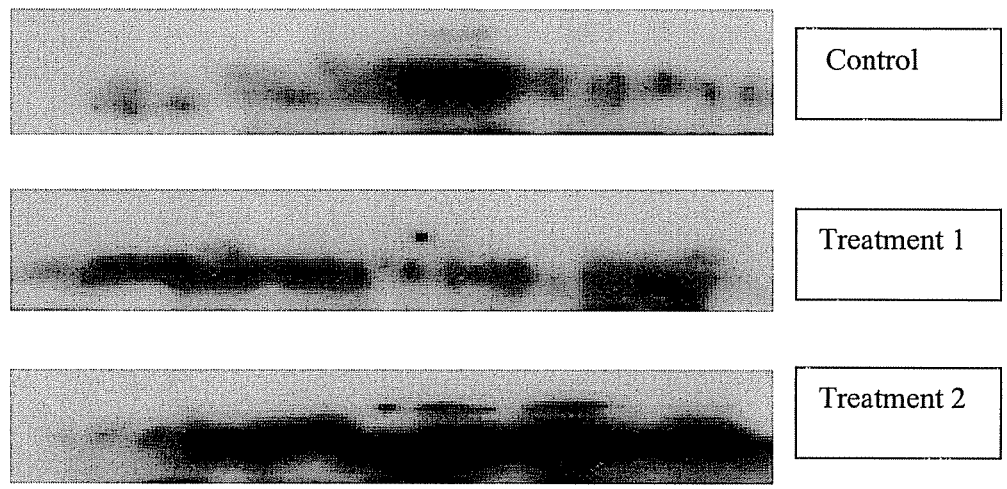
FIG. 8 shows results from Western blotting experiments that demonstrate effects of the composition on expression of neutrophil L-selectin in beef cattle as described in Example 6.

Protein concentrations of neutrophil L-selectin were also assessed using Western blotting as shown in FIG. 8. The mRNA concentration for L-selectin was also determined as for the rat study (Example 4) but using bovine-specific primers. It was determined that both the Treatment 1 (15 g of Experimental composition/head/day) and Treatment 2 (30 g of Experimental composition/head/day) increased ($P<0.05$) concentrations of neutrophil L-selectin compared to the Control treatment.

TABLE 2

| Ingredient | percent of supplement (as feed basis) |
|---|---|
| Cotton hulls | 32.5 |
| Corn | 25.0 |
| Wheat mill run | 6.25 |
| Canola meal | 7.50 |
| Distillers grains | 8.73 |
| Limestone | 0.75 |
| Dynamate | 0.25 |
| Magnesium oxide | 0.15 |
| Alfalfa meal | 14.0 |
| Urea | 0.50 |
| Rumensin | 0.01 |
| Zinc sulphate | 0.01 |
| Selenium | 0.04 |
| Sodium chloride | 0.30 |
| Molasses | 4.00 |

TABLE 3

| Day of study | Control (Abs at 450 nm) | Treatment 1 (Abs at 450 nm) | Treatment 2 (Abs at 450 nm) |
|---|---|---|---|
| 14 days | 0.477 | 0.404 | 0.391 |
| 28 days | 0.736 | 0.409 | 0.424 |
| 42 days | 0.842 | 0.405 | 0.408 |
| 56 days | 1.97 | 0.717 | 1.65 |

TABLE 4

| Day of study | Control (Abs at 450 nm) | Treatment 1 (Abs at 450 nm) | Treatment 2 (Abs at 450 nm) |
| --- | --- | --- | --- |
| 0 days | 0.035 | 0.036 | 0.033 |
| 28 days | 0.065 | 0.045 | 0.035 |
| 42 days | 0.058 | 0.065 | 0.109 |
| 56 days | $0.238^a$ | $0.543^b$ | $0.471^b$ |
| 82 days | $0.033^a$ | $0.549^b$ | $0.573^b$ |

Values within a row which do not share a common superscript differ significantly ($P < 0.05$ threshold).

TABLE 5

| Day of study | Control (Abs at 450 nm) | Treatment 1 (Abs at 450 nm) | Treatment 2 (Abs at 450 nm) |
| --- | --- | --- | --- |
| 0 days | 0.079 | 0.104 | 0.091 |
| 28 days | 0.220 | 0.229 | 0.215 |
| 42 days | 0.228 | 0.296 | 0.358 |
| 56 days | $0.306^a$ | $0.401^a$ | $0.681^b$ |
| 82 days | 0.178 | 0.179 | 0.252 |

Values within a row which do not share a common superscript differ significantly ($P < 0.05$ threshold).

EXAMPLE 7

An experiment was completed with sheep to investigate the ability of the Experimental composition of Example 1 to augment adaptive immunity in response to the J5 *E. coli* vaccination protocol which was employed in Example 6. Animals (twelve animals per treatment) were allotted to three treatments: Control, Treatment 1 (3 grams per head per day of the Experimental composition of Example 1) or Treatment 2 (6 grams per head per day of the Experimental composition of Example 1). Animals were fed these diets for 75 days and were vaccinated with the Pfizer J5 vaccine on Days 7, 21 and 35 of the trial. Blood samples were taken on Days 0, 35 and 75. Blood samples were also taken on Day 90 after the Treatment 1 or Treatment 2 composition had been withdrawn from the diet to determine whether this composition had the ability to maintain titer.

Figure 9:
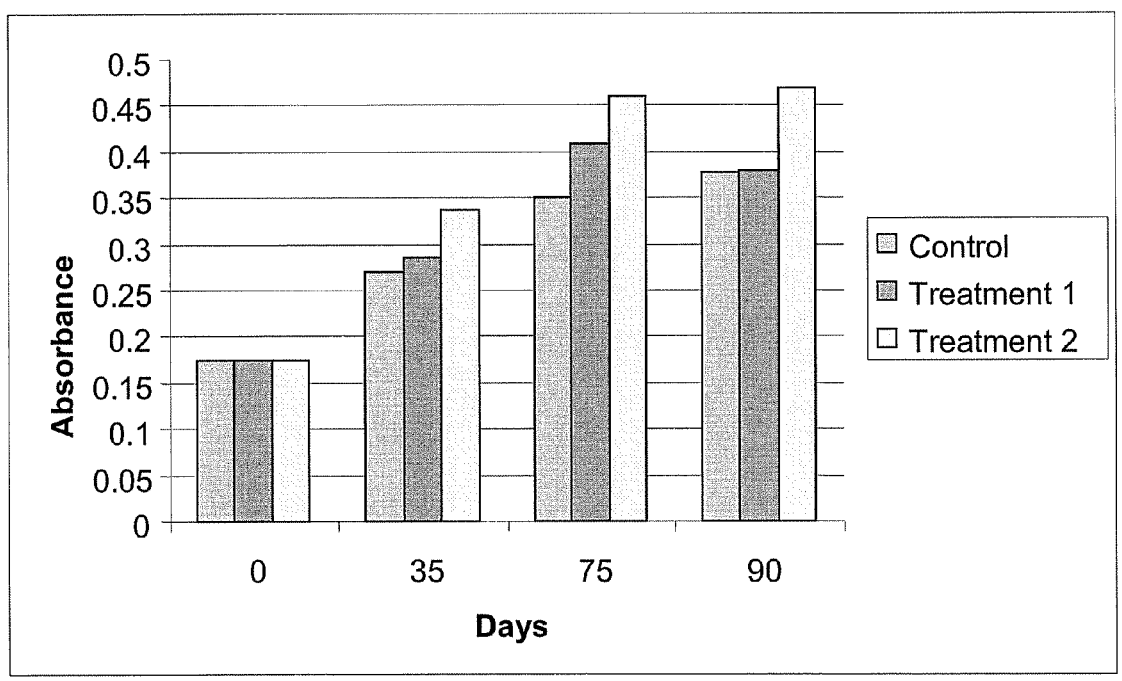
FIG. 9 is a bar graph that summarizes the results of ELISAs used to quantitate the total of the IgG1 and IgG2 titer as described in Example 7.

In this study, a secondary antibody (HRP-conjugated rabbit anti-ovine IgG: Beth Laboratories, Montgomery, Tex.) which recognized both IgG1 and IgG2 sheep isotypes was used. Table 6 and FIG. 9 show data from the combined sheep IgG1 and IgG2 fractions. The methods used in this study to conduct the ELISA were identical to those outlined in Example 6 except that an anti-ovine IgG antibody (VMRD, Pullman, Wash.) was used instead.

On Day 35, the high dose of the Experimental composition caused an elevation in the total of the IgG1 and IgG2 titers. On Day 75, the low and high doses of the Composition caused a step-wise increase in J5 titer. Specifically, the low dose caused a 17% increase in titer and the high dose caused a 31% increase in J5 titer. On Day 90, animals in Treatment 1 did not have an elevation in titer compared to control-fed animals. However, animals in Treatment 2 which received the high dose of the Composition exhibited a 24% elevation in J5 titer.

These data support the observations of Experiment 6 in that administration of the Experimental composition increased development of titer within the IgG1 and IgG2 fraction and maintained titer following withdrawal of the Experimental composition from the diet for an additional 15 days.

TABLE 6

| Day of study | Control (Abs U at 450 nm) | Treatment 1 (Abs U at 450 nm) | Treatment 2 (Abs U at 450 nm) |
| --- | --- | --- | --- |
| 0 days | 0.174 | 0.173 | 0.173 |
| 35 days | 0.270 | 0.285 | 0.336 |
| 75 days | 0.350 | 0.410 | 0.460 |
| 90 days | 0.376 | 0.379 | 0.469 |

The invention tended to increase J5 titer in the combined IgG fractions although the P values were greater than the $P < 0.05$ threshold.

It will be understood that the embodiments of the present composition which have been described are illustrative of some of the applications of the principles of the present composition. Numerous modifications may be made by those skilled in the art without departing from the true spirit and scope of the composition. Various features which are described herein can be used in any combination and are not limited to procure combinations that are specifically outlined herein.

We claim:

1. A combination for enhancing vaccine effectiveness, comprising:
   a vaccine; and
   a mixture comprising an animal feed and from about 0.1 kg to about 20 kg per ton of feed of a composition comprising β-glucans, β-1,3 (4)-endoglucanohydrolase, silica, a mineral clay, and mannans, wherein the composition increases a titer of antibodies to the vaccine relative to the titer of the antibodies in the absence of the composition.

2. The combination of claim 1, wherein the mixture comprises from about 0.5 kg to about 10 kg of the composition per ton of animal feed.

3. The combination of claim 1, wherein the mixture is fed to non-ruminant animals.

4. The combination of claim 1, wherein the mixture is fed to bovine livestock in an amount sufficient that each bovine receives from about 10 grams to about 60 grams per day of the composition.

5. The combination of claim 1, wherein the mixture is fed to sheep in an amount sufficient that each sheep receives from about 2 grams to about 10 grams per day of the composition.

6. The combination of claim 1, wherein the animal feed is a solid feed, a liquid feed, or water.

7. The combination of claim 1, wherein the composition increases a titer of IgG1 or IgG2 antibodies relative to the titer of the IgG1 or IgG2 antibodies in the absence of the composition.

8. The combination of claim 7, wherein the increased titer of the IgG1 or IgG2 antibodies relative to the titer of the IgG1 or IgG2 antibodies in the absence of the composition is maintained after the withdrawal of the composition from the diet of the animals.

9. The combination of claim 1, wherein the silica is obtained from diatomaceous earth.

10. The combination of claim 1, wherein the mannans comprise glucomannan.

11. The combination of claim 10, wherein the silica is obtained from diatomaceous earth, and the composition comprises 0.05-3% β-1,3 (4)-endoglucanohydrolase, 1-40% diatomaceous earth, 1-20% β-1, 3(4) glucan and glucomannan, and 40-92% mineral clay by weight.

12. The combination of claim 1, wherein the vaccine is a vaccine for mastitis, infectious bovine rhinotracheitis, parainfluenza type 3, bovine virus diarrhea virus, bovine respiratory syncytial virus, rota virus, corona virus, *Campylobacter* spp.,

*Pasteurella* spp., pinkeye, *Salmonella* spp., *Clostridium* spp., *Leptospirosis*, brucellosis, Newcastle disease, fowl pox, erysipelas, fowl cholera, Marek's Disease Virus, Infectious Bronchitis Virus, avian encephalomyelitis, coccidiosis, rhinopneumonitis, equine influenza, *Streptococcus equi*, equine viral arteritis, equine monocytis ehrlichiosis, encephalomyelitis, West Nile encephalitis, rabies, parvovirus, adenovirus, *Bordetella*, Lyme disease, *Giardia*, pertussus, measles virus, hepatitis A, hepatitis B, diphtheria, or poliomyelitis.

13. A method for vaccinating an individual, comprising:
administering the combination of claim 1 to an individual of a mammalian species or an avian species, wherein administering the combination comprises
feeding the mixture comprising the animal feed and the composition to the individual prior to administering a dose of the vaccine to the individual, and
vaccinating the individual with the vaccine, wherein the individual subsequently has an increased titer of antibodies to the vaccine relative to a titer of antibodies to the vaccine if the mixture had not been fed to the individual.

14. The method of claim 13, wherein the mixture is fed daily to the individual.

15. The method of claim 13, wherein the mixture comprises from about 0.5 kg to about 10 kg of the composition per ton of animal feed.

16. The method of claim 13, wherein the mammalian species is a non-ruminant.

17. The method of claim 13, wherein the individual subsequently has an increased titer of IgG1 or IgG2 antibodies relative to a titer of the IgG1 or IgG2 antibodies if the composition had not been administered.

18. The method of claim 13 wherein the mixture is fed daily to the individual for at least 7 days prior to administering the dose of the vaccine.

19. The method of claim 13, further comprising feeding the mixture to the individual after administering the dose of the vaccine and prior to administering one or more subsequent doses of the vaccine.

20. The method of claim 13, wherein the vaccine is a vaccine for mastitis, infectious bovine rhinotracheitis, parainfluenza type 3, bovine virus diarrhea virus, bovine respiratory syncytial virus, rota virus, corona virus, *Campylobacter* spp., *Pasteurella* spp., pinkeye, *Salmonella* spp., *Clostridium* spp., *Leptospirosis*, brucellosis, Newcastle disease, fowl pox, erysipelas, fowl cholera, Marek's Disease Virus, Infectious Bronchitis Virus, avian encephalomyelitis, coccidiosis, rhinopneumonitis, equine influenza, *Streptococcus equi*, equine viral arteritis, equine monocytis ehrlichiosis, encephalomyelitis, West Nile encephalitis, rabies, parvovirus, adenovirus, *Bordetella*, Lyme disease, *Giardia*, pertussus, measles virus, hepatitis A, hepatitis B, diphtheria, or poliomyelitis.

* * * * *